US006355832B1

(12) United States Patent
Weferling et al.

(10) Patent No.: US 6,355,832 B1
(45) Date of Patent: Mar. 12, 2002

(54) PROCESSING FOR PREPARING SALTS OF DIALKYLPHOSPHINIC ACIDS

(75) Inventors: Norbert Weferling, Hürth; Hans-Peter Schmitz, Brühl; Günter Kolbe, Kerpen, all of (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/610,953

(22) Filed: Mar. 10, 2000

Related U.S. Application Data

(63) Continuation of application No. 09/198,540, filed on Nov. 24, 1998.

(30) Foreign Application Priority Data

Nov. 28, 1997 (DE) .......................................... 197 52 735
Nov. 10, 1998 (DE) .......................................... 198 51 729

(51) Int. Cl.$^7$ ................................................ C07F 9/30
(52) U.S. Cl. ......................................................... 562/8
(58) Field of Search ...................... 562/8, 133; 524/133

(56) References Cited

U.S. PATENT DOCUMENTS

| | | | | |
|---|---|---|---|---|
| 2,957,931 | A | 10/1960 | Hamilton et al. | ............ 260/403 |
| 3,488,368 | A | 1/1970 | Spivack | .................... 260/429.7 |
| 3,534,127 | A | 10/1970 | Spivack | ...................... 260/968 |
| 3,563,948 | A | 2/1971 | Spivack | .................... 260/45.75 |
| 3,742,096 | A | 6/1973 | Spivack | ...................... 260/953 |
| 3,912,654 | A | 10/1975 | Heid et al. | ............... 252/321 |
| 3,914,345 | A | 10/1975 | Kleiner et al. | ............... 260/970 |
| 4,036,811 | A | 7/1977 | Noetzel et al. | ...... 260/45.75 W |
| 4,208,322 | A | 6/1980 | Sandler | ............... 260/45.75 K |
| 4,321,187 | A | 3/1982 | Granzow | .................... 524/133 |
| 4,590,014 | A | 5/1986 | Wolf et al. | ........... 260/502.4 R |
| 4,632,741 | A | 12/1986 | Wolf et al. | .............. 204/157.73 |
| 4,939,285 | A | 7/1990 | Weis et al. | ............... 558/214 |
| 4,972,011 | A | 11/1990 | Richardson et al. | ......... 524/130 |
| 4,973,727 | A | 11/1990 | Gainer et al. | ............... 558/133 |
| 5,780,534 | A | 7/1998 | Kleiner et al. | ............... 524/133 |
| 6,207,736 | B1 | 3/2001 | Nass et al. | ................... 524/126 |

FOREIGN PATENT DOCUMENTS

| | | |
|---|---|---|
| EP | 0327496 | 8/1989 |
| EP | 0699708 | 3/1996 |
| ES | 8505520 | 5/1984 |
| FR | 1 558 606 A | 2/1969 |

OTHER PUBLICATIONS

Chemical abstracts vol. 64 abstract No. 16661 g by Hoffman (6/66).
Houben–Weyl, Methoden der organischen Chemie, vol. XII/1, 4$^{th}$ Edition, 1963, pp. 228ff.
"Phosphinsaure und deren Derivate," Dr. Felcht, vol. E2, 1982, pp. 123 ff.
E.E. Nifant'ev: "Acid catalysis in the hydrophosphorylation of olefins" Journal of General Chemistry USSR., vol. 50, No. 8/1,—Aug. 1980, pp. 1416–1423, XP002093427, New York US.
E.E. Nifant'ev: "Hydrophosphorylation of cyclopentenes" Journal of General Chemistry USSR., vol. 61, No. 1/1,— Jan. 1991 pp. 83–92, XP002093428 New York US.
Chemical Abstracts, vol. 69, No. 16, Oct. 14, 1968 Columbus, OH, US; abstract No. 067487, p. 6310; col. 2; XP002093429 & Petrov K.A.: "Dialkylphosphinic acids" Khim. Org. Soedin. Fosfora, Akad. Nauk SSSR, Otd. Obshch. Tekh. Khim., 1967, pp. 181–186, SU.
Synthesis of DI(n–octyl)phosphinic acid. Influence of the sulfuric acide in the phosphination of 1–octene with sodium hypophosphite, M. Martinez, C. Herranz, N. Miralles, & A. Sastre, AFINIDAD LII, 466, 1996, pp. 404–406.
CA:107:25119 abs of ES532346 (6/85).
CA:107:176590 abs of Bull Chem Soc Jpn by Ohno 60 (8) pp 2945–51 (1987).
William C. Drinkard: "Some salts of symmetric phosphinic acids" Journal of the American Chemical Society., Bd. 74, Nr. 21, –5. Nov. 1952 Seiten 5520–5521, XP002093391.

*Primary Examiner*—Jean F. Vollano
(74) *Attorney, Agent, or Firm*—Susan S. Jackson; Scott E. Hanf

(57) ABSTRACT

The invention relates to a process for preparing salts of dialkylphosphinic acids, which comprises
  a) reacting alkylphosphonous and/or hypophosphorous acid and/or alkali metal salts thereof with olefins in the presence of a free-radical initiator to give dialkylphosphinic acids and/or alkali metal salts thereof and
  b) reacting the dialkylphosphinic acids and/or alkali metal salts thereof obtained according to a) with metal compounds of Mg, Ca, Al, Sb, Sn, Ge, Ti, Zn, Fe, Zr, Ce, Bi, Sr, Mn, Li, Na and/or K to give the metal dialkylphosphinate salts. The invention likewise relates to the use of the metal dialkylphosphinate salts prepared by the process according to the invention for preparing flame retardants.

19 Claims, No Drawings

PROCESSING FOR PREPARING SALTS OF DIALKYLPHOSPHINIC ACIDS

CROSS-REFERENCES TO RELATED APPLICATIONS

This application is a continuation of application Ser. No. 09/198,540, filed Nov. 24, 1998, which is herein incorporated by reference.

FIELD OF THE INVENTION

The invention relates to a process for preparing salts of dialkylphosphinic acids and to the use of the dialkylphosphinate salts prepared by this process.

BACKGROUND OF THE INVENTION

Aluminum salts of organic phosphorus-containing acids are known as flame retardants. They can be prepared by various processes.

EP-A-0 299 922 describes a process for preparing aluminum salts of phosphoric and phosphonic esters by reacting aluminum with phosphoric acid, phosphonic acid or an ester thereof.

In the process described in EP-A-0 245 207, aluminum compounds are reacted with alkylphosphonic diesters to give the corresponding aluminum salt.

According to EP-A-0 327 496, the reaction of aluminum hydroxide with alkylphosphonic diesters in the absence of water at approximately 180° C. likewise leads to aluminum salts of phosphnic half-esters.

EP-A-0 699 708 describes flame-retardant polyester molding compounds, the polyesters being given a flame-retardant finish by adding calcium salts or aluminum salts of phosphinic or diphosphinic acids. The above-mentioned salts are obtained by reacting the corresponding dialkylphosphinic acids with calcium hydroxide or aluminum hydroxide.

DE 24 47 727 describes low-flammability polyamide molding compounds which comprise a salt of a phosphinic acid or of a diphosphinic acid.

However, the abovementioned processes have the disadvantage that the suitable organic phosphorus compounds must first be prepared in a laborious manner. This applies, in particular, to the dialkylphosphinic acids, whose aluminum salts give the best results in the application as flame retardants, and for which, likewise, some synthetic pathways are described.

Thus DE 21 00 779 A1 describes a process for preparing alkyl dialkylphosphinates by addition of olefins having from 2 to 22 carbon atoms to alkylphosphonous esters.

In this case also, there has been the lack to date of an economic synthesis method which leads to homogeneous products in a high yield.

SUMMARY OF THE INVENTION

The object therefore underlying the invention is to provide a process for preparing salts of dialkylphosphinic acids in which, in a particularly simple and economical manner, not only the dialkylphosphinic acids and/or their alkali metal salts, but also the desired end products, that is to say dialkylphosphinic salts of certain metals, may be prepared.

This object is achieved by a process of the type described at the outset, which comprises
   a) reacting alkylphosphonous and/or hypophosphorous acid and/or alkali metal salts thereof with olefins in the presence of a free-radical initiator to give dialkylphosphinic acids and/or alkali metal salts thereof and
   b) reacting the dialkylphosphinic acids and/or alkali metal salts thereof obtained according to a) with metal compounds of Mg, Ca, Al, Sb, Sn, Ge, Ti, Zn, Fe, Zr, Ce, Bi, Sr, Mn, Li, Na and/or K to give the metal dialkylphosphinate salts.

DESCRIPTION OF THE PREFERRED EMBODIMENTS

Preferably, as free-radical initiator, use is made of azo compounds.

Preferably, the azo compounds are cationic and/or non-cationic azo compounds.

Preferably, as cationic azo compounds, use is made of 2,2'-azobis(2-amidinopropane)dihydrochloride or 2,2'-azobis(N,N'-dimethyleneisobutyramidine)dihydrochloride.

Preferably, as non-cationic azo compounds, use is made of azobis(isobutyronitrile), 4,4'-azobis(4-cyanopentanoic acid) or 2,2'-azobis(2-methylbutyronitrile).

Preferably, as free-radical initiator, use is made of inorganic peroxide free-radical initiators and/or organic peroxide free-radical initiators.

Preferably, as inorganic peroxide free-radical initiator, use is made of hydrogen peroxide, ammonium peroxodisulfate and/or potassium peroxodisulfate.

Preferably, as organic peroxide free-radical initiators, use is made of dibenzoyl peroxide, di-tert-butyl peroxide and/or peracetic acid.

A wide selection of suitable free-radical initiators is found, for example, in Houben-Weyl, Supplementary Volume 20, in the chapter "Polymerisation durch radikalische Initiierung" [Polymerization by Free-Radical Initiation] on pages 15–74.

Preferably, the metal compounds are metal oxides, metal hydroxides, metal hydroxide oxides, metal sulfates, metal acetates, metal nitrates, metal chlorides and/or metal alkoxides.

Particularly preferably, the metal compounds are aluminum hydroxide or aluminum sulfates.

Preferably,
   a) alkali metal salts of hypophosphorous acid are reacted with olefins in the presence of a cationic free-radical initiator to give the alkali metal dialkylphosphinates and
   b) the alkali metal dialkylphosphinates obtained according to a) are reacted with aluminum compounds to give the aluminum dialkylphosphinate salts.

Instead of the alkali metal salts of hypophosphorous acid, an aqueous solution of the free acid can likewise be used without problems.

Preferably, the product mixture obtained according to step a) is reacted with the metal compounds without further purification.

In a further embodiment of the process, the product mixture obtained according to step a) is worked up and thereafter only the dialkylphosphinic acids and/or alkali metal salts thereof obtained according to step a) are reacted with the metal compounds.

Preferably, as olefins, use is made of unbranched or branched α-olefins.

Preferably, as olefins, use is made of those having an internal double bond, cyclic or open-chain dienes and/or polyenes having from 2 to 20 carbon atoms.

Preferably, as olefins, use is made of ethylene, n-propylene, isopropylene, n-butene, isobutene, n-pentene, isopentene, n-hexene, isohexene, n-octene, isooctene, 1-decene, 1,5-cyclooctadiene, 1,3-cyclopentadiene, dicyclopentadiene and/or 2,4,4-trimethylpentene isomer mixture.

Preferably, the olefins bear a functional group.

Suitable olefins are compounds of the formula

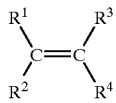

where $R^1$–$R^4$ can be identical or different and are hydrogen, an alkyl group having from 1 to 18 carbon atoms, phenyl, benzyl or alkyl-substituted aromatics.

Suitable olefins are likewise cycloolefins of the formula

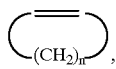

in particular cyclopentene, cyclohexene, cyclooctene and cyclodecene.

Use can also be made of open-chain dienes of the formula

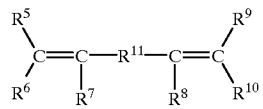

where $R^5$–$R^{10}$ are identical or different and are hydrogen or a $C_1$–$C_6$ alkyl group and $R^{11}$ is $(CH_2)_n$ where n=0 to 6. Preference is given in this case to butadiene, isoprene and 1,5-hexadiene.

Preferred cyclodienes are 1,3-cyclopentadiene, dicyclopentadiene and 1,5-cyclooctadiene, and also norbornadiene.

Preferably, the alkylphosphonous acid and/or alkali metal salts thereof are methylphosphonous acid or methylphosphonous acid and/or alkali metal salts thereof.

Preferably, the reaction in step a) is carried out at a temperature of from 40 to 130° C.

Particularly preferably, the reaction in step a) is carried out at a temperature of from 70 to 110° C.

Preferably, the reaction in step b) is carried out at a temperature of from 20 to 150° C.

Particularly preferably, the reaction in step b) is carried out at a temperature of from 80 to 120° C.

Preferably, the reactions in step a) and in step b) are carried out in an acetic acid medium.

In step b), preference is also given to reaction in aqueous medium.

In this case, the reaction in step b) is carried out after adjusting to a pH range for the salt precipitation which is optimum for the respective system of dialkylphosphinic acid/metal compound.

The present invention also relates in particular to a process in which sodium hypophosphite is reacted with ethylene in the presence of a cationic or non-cationic free-radical initiator or in the presence of a peroxide free-radical initiator to give the sodium salt of diethylphosphinic acid as main product.

This product is then reacted according to the invention with aluminum hydroxide or an aluminum sulfate to give the aluminum salt of diethylphosphinic acid.

The invention also relates to the use of the metal, dialkylphosphinate salts prepared by the process according to the invention for preparing flame retardants.

In particular, the invention relates to the use of the metal dialkylphosphinate salts prepared according to the invention for preparing flame retardants for thermoplastic polymers such as poly(ethylene terephthalate), poly(butylene terephthalate), polystyrene or polyamide and for thermosetting plastics.

Finally, the invention also relates to the use of metal dialkylphosphinate salts prepared by the process according to the invention as additives in polymeric molding compounds.

The invention is described in more detail by the examples below.

EXAMPLE 1 a) Preparation of Methylethylphosphinic Acid 1000 g (12.5 mol) of methylphosphonous acid were introduced into an autoclave together with 50 g (0.18 mol, 1.5 mol %) of 2,2'-azobis(2-amidinopropane) dihydrochloride and the mixture was first heated to 60° C. with stirring. Thereafter, ethylene was introduced into the reactor up to saturation at a pressure of 20 bar. After a reaction time of 17 h at a maximum of 81° C., the reactor was depressurized and cooled. The yield was 1.35 kg.

| $^{31}$P-NMR analysis: | Methylethylphosphinic acid: | 92.4 mol % |
|---|---|---|
| | Methylbutylphosphinic acid: | 6.2 mol % |
| | Methylphophonous acid: | 0.9 mol % |
| | Unknown components: | 0.5 mol % | b) Preparation of the Aluminum Salts 1100 g of the mixture obtained according to a) predominantly comprising methylethylphosphinic acid and methylbutylphosphinic acid were dissolved in 2800 ml of acetic acid and 270 g (3.4 mol) of aluminum hydroxide were added. The mixture was heated for 5 hours under reflux, then cooled, filtered off by suction and dried in a vacuum drying cabinet at 135° C. In total, 1172 g of product were obtained, corresponding to a yield of 97%. The content of aluminum methylethylphosphinate was 93.2 mol % and of aluminum methylbutylphosphinate was 6.1 mol %.

EXAMPLE 2 a) Preparation of Diethylphosphinic Acid (as Sodium Salt)

2.2 kg (20.7 mol) of sodium hypophosphite monohydrate were dissolved in 8 kg (7.62 l) of acetic acid and introduced into an enamel steel 16 l jacketed pressure reactor. After heating the reaction mixture up to 85° C., ethylene was introduced into the reactor up to saturation via a reducing valve set to 5 bar. The reaction was started by adding a solution of 56 g (1 mol %) of 2,2'-azobis(2-amidinopropane) dihydrochloride in 250 ml of water with constant stirring and was controlled via the rate of addition of free-radical initiator in such a manner that the reaction temperature in the reactor did not exceed 95° C. at a jacket temperature of 80° C. with constant addition of ethylene at a mean pressure of about 5 bar. The metering time was in total 3 hours. The mixture was then given a post-reaction time of a further 3 h at 85° C. The reactor was depressurized, cooled to room temperature and the contents were analyzed.

| $^{31}$P-NMR analysis: | Sodium diethylphosphinate: | 87.0 mol % |
|---|---|---|
| | Sodium ethylbutylphosphinate: | 11.9 mol % |
| | Sodium monoethylphosphinate: | 0.9 mol % |
| | Sodium hypophosphite: | 0.1 mol % |
| | Unknown components: | 0.1 mol % |

The total amount of the contents was 11.7 kg. This is equivalent to an ethylene uptake of 1.2 kg (100% of theory).

b) Preparation of the Aluminum Diethylphosphinate Salt 800 g of the mixture of principally sodium diethylphosphinate obtained according to a) were dissolved in 2500 ml of acetic acid and then 38 g (0.48 mol) of aluminum hydroxide were added. The mixture was then heated for about 4 hours under reflux, cooled and filtered off. The resulting solids were first washed with 1 liter of glacial acetic acid, then with 1 liter of distilled water and finally with 500 ml of acetone, and then dried under reduced pressure at 130° C. Yield: 183 g (92% of theory).

EXAMPLE 3 a) Preparation of Diethylphosphinic Acid (Sodium Salt)

2.12 kg (20 mol) of sodium hypophosphite monohydrate were dissolved in 7 kg of acetic acid and introduced into an enamel steel 16 l jacketed pressure reactor. After heating the reaction mixture to 100° C., ethylene was introduced into the reactor up to saturation via a reducing valve set to 5 bar. A solution of 32.8 g (1 mol %) of azobis(isobutyronitrile) (AIBN) in 500 g of acetic acid was added uniformly in the course of a period of 6 h with constant stirring at an ethylene pressure of 5 bar and at a temperature of 100–105° C. After a post-reaction time of 1 h, depressurization of the reactor and cooling to room temperature, the contents were analysed:

| $^{31}$P-NMR: | Sodium diethylphosphinate: | 91.3 mol % |
|---|---|---|
| | Sodium butylethylphosphinate: | 7.7 mol % |
| | Sodium ethylphosphonite: | 0.7 mol % |
| | Unknown components: | 0.3 mol % |

The ethylene uptake was 1160 g (100% of theory).

b) Preparation of the Aluminum Diethylphosphinate Salt 520 g (6.67 mol) of aluminum hydroxide were added to the solution obtained according to a), the mixture was heated for 4 h at 80° C. and refluxed for a further 4 h. The solids obtained were then filtered off, washed twice, each time with 2 l of acetic acid and 2 l of water one after the other, and dried under reduced pressure at 130° C. Yield: 2210 g (85% of theory).

EXAMPLE 4 a) Preparation of Diethylphosphinic Acid

A mixture of 2.64 kg (20 mol) of a 50% strength aqueous solution of hypophosphorous acid and 7 kg of acetic acid was introduced into an enamel steel 16 l jacketed pressure reactor. After heating the reaction mixture up to 100° C., ethylene was introduced into the reactor up to saturation via a reducing valve set to 5 bar. A solution of 56 g (1 mol %) of 4,4'-azobis(4-cyanopentanoic acid) in 500 g of acetic acid was added uniformly in the course of a period of 6 h with constant stirring at an ethylene pressure of 5 bar and a temperature of 100–105° C. After a post-reaction time of 1 h, depressurization of the reactor and cooling to room temperature, the contents were analysed:

| $^{31}$P-NMR: | Diethylphosphinic acid: | 90.6 mol % |
|---|---|---|
| | Butylethylphosphinic acid: | 8.4 mol % |
| | Ethylphosphonous acid: | 0.8 mol % |
| | Unknown components: | 0.2 mol % |

The ethylene uptake was 1160 g (100% of theory).

b) Preparation of the Aluminum Diethylphosphinate Salt

The solution obtained according to a) was very largely freed from the solvent acetic acid on a rotary evaporator and then 10 l of water were added. 4500 g (3.5 mol) of a 46% strength aqueous solution of $Al_2(SO_4)_3 \cdot 14H_2O$ were added in the course of one hour. The resulting solids were then filtered off, washed twice each time with 2 l of acetic acid and 2 l of water one after the other, and dried at 130° C. under reduced pressure. Yield: 2520 g (82% of theory).

EXAMPLE 5 a) Preparation of Dioctylphosphinic Acid (Sodium Salt)

A solution of 1.5 g (2 mol %) of 2,2'-azobis(2-methylbutyronitrile) in 50 g of acetic acid were added uniformly in the course of a period of 16 h at 95° C. with constant vigorous stirring to a mixture of 42.4 g (0.4 mol) of sodium hypophosphite monohydrate, 134.4 g (1.2 mol) of 1-octene and 1 kg of acetic acid in a 2 l three-neck flask fitted with stirrer, reflux condenser and metering apparatus. After a post-reaction time of 1 h and cooling to room temperature, the contents were analysed:

| $^{31}$P-NMR: | Dioctylphosphinic acid: | 94.1 mol % |
|---|---|---|
| | Hexadecyloctylphosphinic acid: | 4.2 mol % |
| | Octylphosphonous acid: | 1.1 mol % |
| | Unknown components: | 0.6 mol % | b) Preparation of the Aluminum Dioctylphosphinate Salt 10.4 g (0.13 mol) of aluminum hydroxide were added to the solution obtained according to a), heated for 4 h at 80° C. and refluxed for a further 16 h. The resulting solids were then filtered off, washed twice each time with 200 ml of acetic acid and 200 ml of water one after the other and dried at 130° C. under reduced pressure. Yield: 90 g (75% of theory).

What is claimed is:

1. A process for preparing salts of dialkylphosphinic acids, which comprises
    a) reacting alkylphosphonous and/or hypophosphorous acid and/or alkali metal salts thereof with olefins in the presence of a free-radical initiator, wherein the free-radical initiator is an azo-compound, to give dialkylphosphinic acids and/or alkali metal salts thereof and
    b) reacting the dialkylphosphinic acids and/or alkali metal salts thereof obtained according to a) with metal compounds of Mg, Ca, Al, Sb, Sn, Ge, Ti, Zn, Fe, Zr, Ce, Bi, Sr, Mn, Li, Na and/or K to give the metal dialkylphosphinate salts.

2. The process as claimed in claim 1, wherein the azo compound is a cationic azo compound or a non-cationic azo compound.

3. The process as claimed in claim 2, wherein the cationic azo compound is 2,2'-azobis(2-amidinopropane) dihydrochloride or 2,2'-azobis(N,N'-dimethyleneisobutyramidine)dihydrochloride.

4. The process as claimed in claim 2, wherein the non-cationic azo compound is azobis(isobutyronitrile), 4,4'-azobis(4- cyanopentanoic acid) or 2,2'-azobis(2-methylbutyronitrile).

5. The process as claimed in claim 1, wherein the metal compounds are metal oxides, metal hydroxides, metal hydroxide oxides, metal sulfates, metal acetates, metal nitrates, metal chlorides and/or metal alkoxides.

6. The process as claimed in claim 1, wherein the metal compounds are aluminum hydroxide or aluminum sulfates.

7. The process as claimed in claim 1, wherein
    a) alkali metal salts of hypophosphorous acid are reacted with olefins in the presence of a cationic free-radical initiator to give the alkali metal dialkylphosphinates and b) the alkali metal dialkylphosphinates obtained according to a) are reacted with aluminum compounds to give the aluminum dialkylphosphinate salts.

8. The process as claimed in claim 1, wherein the product mixture obtained according to step a) is reacted with metal compounds without further purification.

9. The process as claimed in claim 1, wherein the product mixture obtained according to step a) is worked up and thereafter only the dialkylphosphinic acids and/or alkali metal salts thereof obtained according to step a) are reacted with the metal compounds.

10. The process as claimed in claim 1, wherein, as olefins, use is made of unbranched or branched α-olefins.

11. The process as claimed in claim 1, wherein, as olefins, use is made of those having an internal double bond, cyclic or open-chain dienes and/or polyenes having from 4 to 10 carbon atoms.

12. The process as claimed in claim 1, wherein, as olefins, use is made of ethylene, n-proplyene, isopropylene, n-butene, isobutene, n-pentene, isopentene, n-hexene, isohexene, n-octene, isooctene, 1-decene, 1,5-cyclooctadiene, 1,3-cyclopentadiene, dicyclopentadiene and/or 2,4,4-trimethylpentene isomer mixture.

13. The process as claimed in claim 1, wherein the olefins bear a functional group.

14. The process as claimed in claim 1, wherein the alkylphosphonous acid and/or alkali metal salts thereof are methylphosphonous acid or ethylphosphonous acid and/or alkali metal salts thereof.

15. The process as claimed in claim 1, wherein the reaction in step a) is carried out at a temperature of from 40 to 130° C.

16. The process as claimed in claim 1, wherein the reaction in step a) is carried out at a temperature of from 70 to 110° C.

17. The process as claimed in claim 1, wherein the reaction in step b) is carried out at a temperature of from 20 to 150° C.

18. The process as claimed in claim 1, wherein the reaction in step b) is carried out at a temperature of from 80 to 120° C.

19. The process as claimed in claim 1, wherein the reactions in step a) and in step b) are carried out in an acetic acid medium.

* * * * *